United States Patent [19]
Hecht et al.

[11] 3,975,513
[45] Aug. 17, 1976

[54] SUSTAINED-RELEASE TABLET FOR PROPHYLAXIS AGAINST TRACE ELEMENT DEFICIENCY DISEASES

[75] Inventors: Horstmar Hecht, Castrop-Rauxel; Wolfgang Laue, Waltrop; Manfred Kirchgebner, Freising-Weihenstephan, all of Germany

[73] Assignee: Gewerkschaft Victor Chemische Fabrik, Castrop-Rauxel, Germany

[22] Filed: Aug. 30, 1974

[21] Appl. No.: 502,123

[30] Foreign Application Priority Data
Sept. 6, 1973 Germany............................ 2344884

[52] U.S. Cl.................................. 424/19; 424/21; 424/22; 424/147; 424/295
[51] Int. Cl.$^2$...................... A61K 9/24; A61K 9/32; A61K 9/58; A61K 33/26
[58] Field of Search .............................. 424/19–22, 424/147, 295

[56] References Cited
UNITED STATES PATENTS

| | | | |
|---|---|---|---|
| 3,012,937 | 12/1961 | Schlichting ..................... | 424/147 X |
| 3,027,303 | 3/1962 | Wolcott .......................... | 424/147 X |
| 3,056,724 | 10/1962 | Marston ............................... | 424/22 |
| 3,081,233 | 3/1963 | Enz et al ............................ | 424/20 X |
| 3,259,500 | 7/1966 | Barnhart et al ................. | 424/295 X |
| 3,317,394 | 5/1967 | Fryklof et al ........................ | 424/22 |
| 3,428,457 | 2/1969 | Hutchinson ......................... | 424/295 |
| 3,594,469 | 7/1971 | Whitehead et al ............. | 424/147 X |
| 3,822,343 | 7/1974 | Hill et al ............................. | 424/22 |
| 3,823,228 | 7/1974 | Ferris et al ........................... | 424/35 |
| 3,873,588 | 3/1975 | Osawa et al ..................... | 424/295 X |

Primary Examiner—Shep K. Rose
Attorney, Agent, or Firm—Burgess, Dinklage & Sprung

[57] ABSTRACT

For the treatment of trace element deficiency in animals over a prolonged period of time there is orally administered a tablet containing said trace element in a composition which releases said trace element slowly in the stomach of said animal, said tablet having a minimum dimension such that it cannot leave the stomach through the pylorus during said prolonged period of time. For animals such as piglets, about 3 mm is a suitable minimum dimension. The tablet may comprise a homogeneous mixture of a slow release substance and the trace element and/or there may be a slow release coating on the tablet, such as a polymer of vinylidene chloride, an acrylic acid ester, vinyl chloride or vinyl propionate.

7 Claims, 3 Drawing Figures

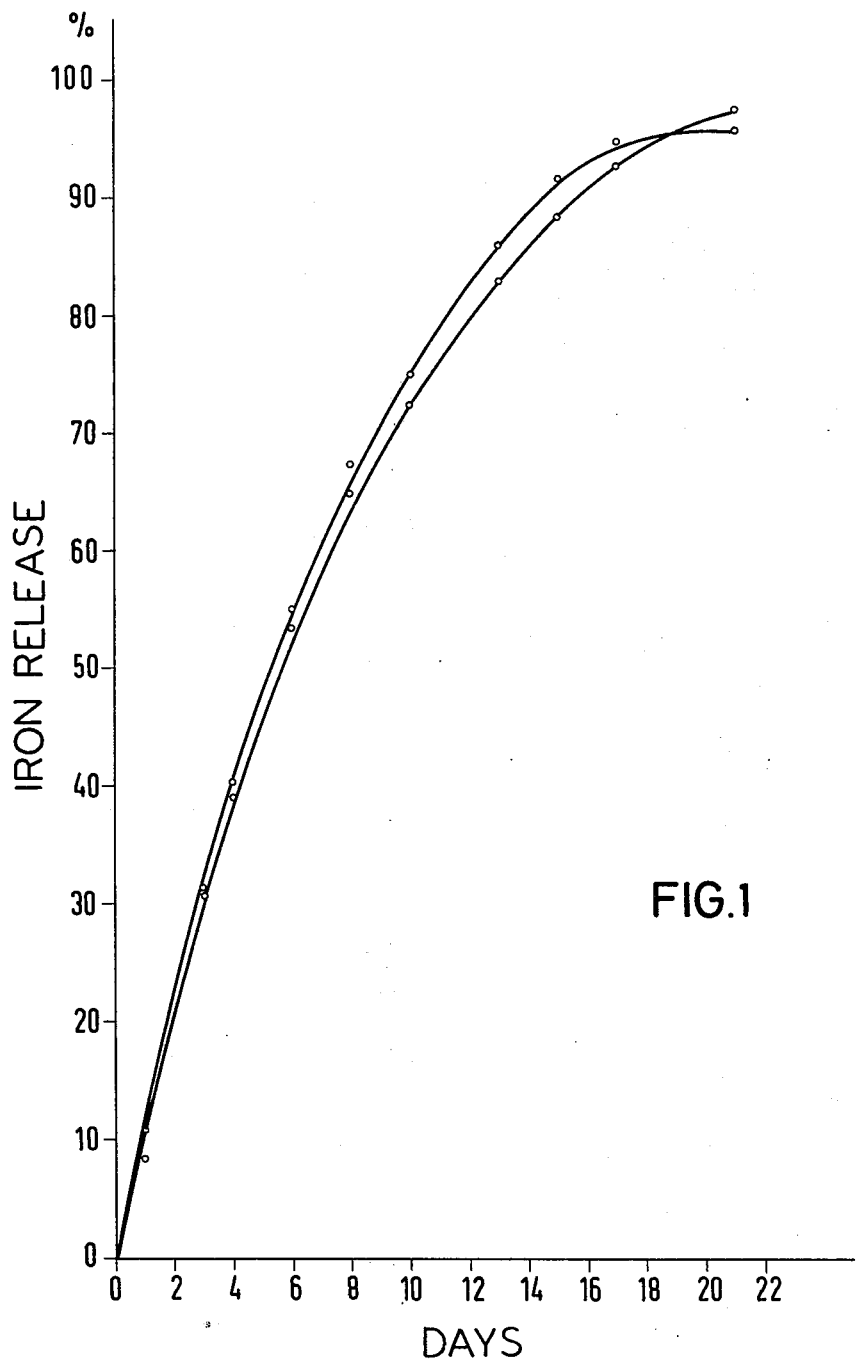

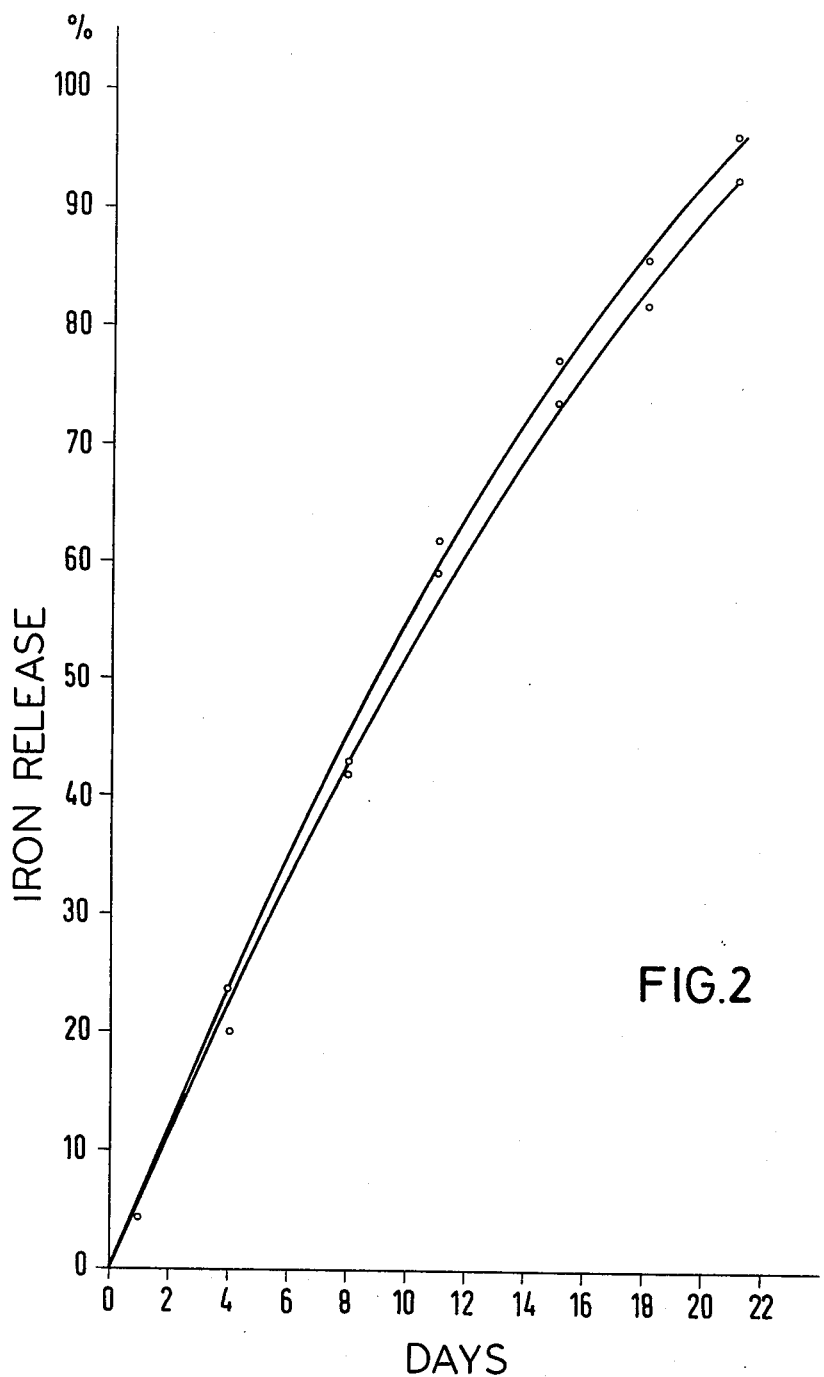

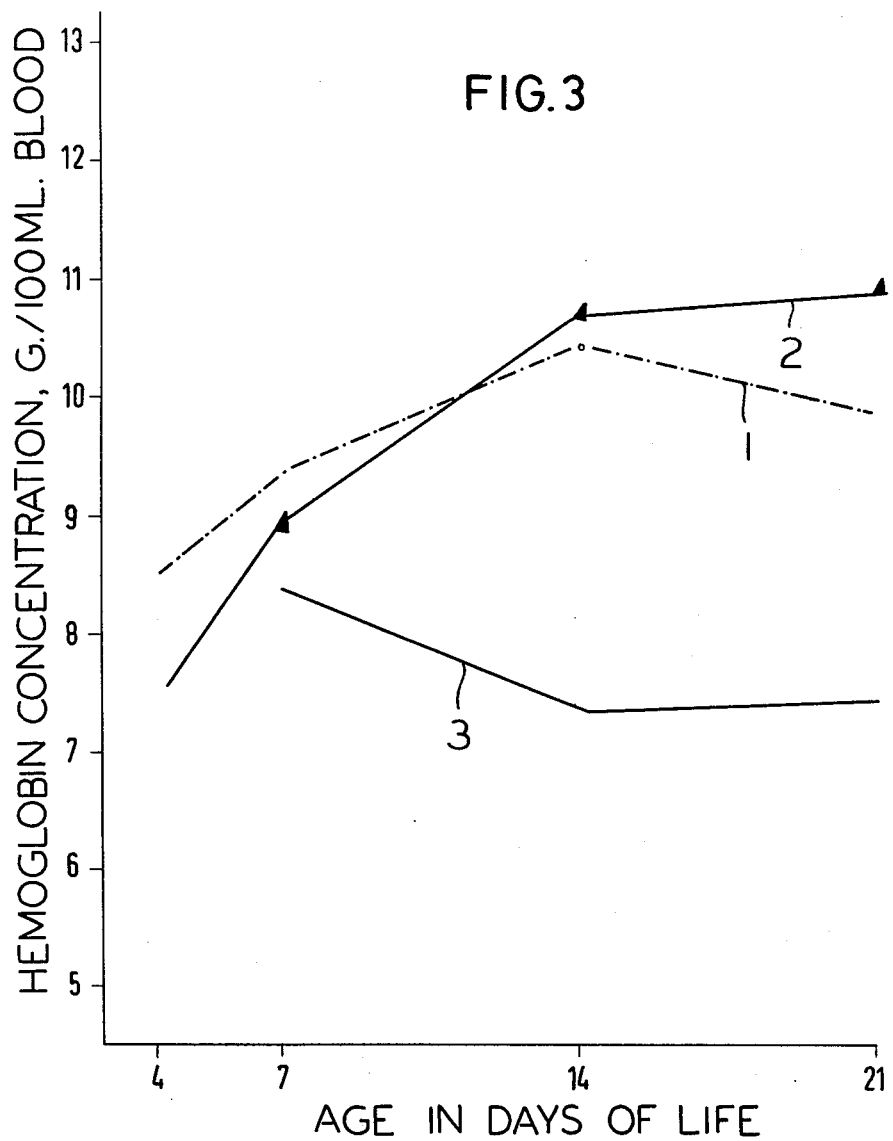

SUSTAINED-RELEASE TABLET FOR PROPHYLAXIS AGAINST TRACE ELEMENT DEFICIENCY DISEASES

BACKGROUND

According to the teachings of modern nutritional science, the absence or insufficiency of trace elements such as iron, copper, manganese, zinc, selenium, fluorine and cobalt in the fodder of young animals leads to deficiency diseases which can be prophylactically prevented or even therapeutically eliminated by the administration of these trace elements. Thus it has been found in the practice of conventional methods of animal husbandry that suckling pigs, for example, do not attain the desired gains during the first phase of their rapid growth if their supply of iron is insufficient. In such cases anemia occurs, which is manifested by an excessively small amount of red blood corpuscles in the blood or of the red blood pigment, hemoglobin, contained in the red blood corpuscles. The young animals are more sensitive to infectious diseases as a result of this imbalance in the blood.

Deficiency diseases which occur in practice, and the trace elements involved therein, are named in M. Kirchgessner's "Wirkstoffe in der praktischen Tierernährung," Bayer. Landwirtschaftsverlag, Munich, 1966. In the case of swine anemia it is possible to remedy the iron deficiency responsible therefor by the parenteral injection of liquid iron preparations, such as aqueous iron-dextran complexes, for example.

The administration of iron salts can also achieve positive results. However, since the yound consume mainly mother's milk in the first days of life, it would be necessary to administer iron salt separately daily for an extended period of time—for the first 21 days of life in the case of piglets, for example. In large-scale hog raising operations, however, this is utterly impractical.

THE INVENTION the invention is addressed to the problem of creating a sustained-release tablet, commonly called a "bolus," for prophylaxis against deficiency diseases due to the lack of trace elements in the diet, which can be administered orally, and which will assure a uniform release of the required amounts of trace elements over the desired period of treatment. In accordance with the invention this can be achieved if the orally administered bolus will, on account of its dimensions, remain in the stomach or intestinal tract during the necessary period of treatment, and contains the trace elements in a form which will assure a substantially uniform release of the trace elements under the physiological chemical conditions in the stomach or intestinal tract during the treatment period.

The sustained-release bolus is of such dimensions, in accordance with the invention, that it can be administered to the animal orally, passing easily through the animal's esophagus, but on account of its size it must be unable to leave the stomach through the pylorus until it has served its sustained-release nutritional purpose. The size of the bolus is to be selected according to the type of animal and stage of growth, the cross-sectional shape being, as a rule, unimportant. It will be best to select a rounded shape in accordance with the shape of the esophagus of the animals being treated; boluses of oblong shape having more active substance for a given diameter have proven especially effective.

The sustained-release bolus may be composed entirely of one of the active trace elements and/or its compounds, or these may be provided as a whole with a coating which retards the release of the ions, or they may be embedded in the form of individual particles in an inert mass, or they may be applied to an inert supporting substance of large surface area.

Trace elements which are lacking and are to be replaced by the sustained-release bolus of the invention are especially iron, manganese, copper, zinc, cobalt, selenium and fluorine. The base metals in unbound form can also serve as the sole source of trace element ions, since they dissolve under the physiological chemical conditions in the stomach. Sustained-release boluses which consist substantially of the elemental trace elements can best have an open-pore structure—a sponge-like structure for example—thus making a larger active surface available to the gastric acid for dissolution. Often it is advantageous to dragee the bolus so as to provide it with a smooth coating to facilitate administration, which will be dissolved in the stomach, or, if it is sufficiently permeable to the gastric juices and trace metal ions, will remain unaltered.

An open-pore structure may also be advantageous when the sustained-release bolus of the invention contains the trace elements also in chemically bound form, e.g., in the form of sparingly soluble salts. However, their solubility must not be so low as to prevent adequate decomposition in the stomach. Examples of suitable salts are: iron-III-diphosphate, iron-II-ammonium phosphate, iron-II-phosphate-8-hydrate (vivianite), iron-III-phosphate-2-hydrate, conserves of iron-II-chloride and sodium polyphosphate, copper-II-diphosphate, copper-II-triphosphate.

It has been found that boluses containing a salt can be mechanically stabilized by a content of the corresponding metal powder. This also makes it possible to control the rate of dissolution and thus adjust it to an optimum value.

A control of the rate of dissolution in the stomach can be achieved not only through the physical structure of the bolus but also through the application of a covering which retards attack by the gastric acid and/or the release of the trace metal ions. Coverings which provide these properties include, for example, thermoplastic polymers, such as vinylidene chloride-acrylic acid ester copolymer, and vinyl chloride copolymers and vinyl propionate copolymers.

These can be applied in the form of aqueous dispersions, for example. The covering at the same time improves the mechanical strength of the bolus and also permits the use of readily soluble salts of the trace elements. The coverings produced from plastic dispersions as a rule produce a dense protective coating in the dry state, while in the stomach they swell and acquire the desired permeability.

The release of the trace metal ions at the desired retarded rate can also be brought about by embedding the trace elements or their compounds in the form of small particles in a ground mass of physiological compatible plastics like those mentioned above.

Lastly, they can be applied to an inert supporting material of large surface area so as to be in a form in which they cannot leave the stomach during the desired period of treatment. The support material can be selected so that it, too, is gradually dissolved, so that the remains of the sustained-release bolus will be able, at the end of the desired time of stay in the stomach of the animal, to leave the stomach through the pylorus. This requirement is fulfilled, for example, by products in which iron particles are embedded in a sponge of calcium polyphosphate, the rate of dissolution of the porous support being able to be regulated by the applied trace metals and/or their compounds or the above-named plastics.

On the basis of the above teaching, the expert is placed in a position to appropriately combine the above-named possibilities for the uniform release of the trace element ions and for the retention of the bolus during the required treatment period in the animal's stomach, and to adapt them to the needs of animals displaying deficiencies of trace elements, and to use them also in human medicine.

The sustained-release bolus can e administered to animals even on the first day of life. It is better, however, to delay application for a few days until the young are sufficiently strong—until the third day in the case of suckling pigs, for example. The most important period for treatment in this case is the first 21 days of life. As a precautionary measure, a bolus will be selected which will provide a supply of trace elements for a few days longer. In other animals, other periods of time, with which the expert is familiar, will be used.

At the end of the desired treatment period the bolus will leave through the pylorus of the stomach, either because it has sufficiently shrunken in volume or because the remaining body, consisting mainly of plastic material, falls apart, and if the bolus or parts thereof dwell further on in the intestinal tract they can assure a supply of the required amount of iron. If such deformation is impossible due to retained strength, this will constitute no danger to the animal, for in that case the remainder will be excreted in a later stage of growth.

The term "tablet" or "bolus" as used herein is not to be interpreted strictly; it is intended to cover any pills in which the powdered active substances alone or together with conventional additives are pressed in tableting machines to form lozenges or any other shapes, and also to cover pills, pastilles, coated tablets, etc., made by other known processes.

As it can be seen from the examples, the tests in vitro, and the animal experiments, the sustained-release bolus of the invention assures the animals of a uniform supply of trace element ions. Additionally, it offers the special advantage that the producer himself can undertake the necessary treatment of young animals with trace elements by including the sustained-action tablet of the invention in the diet, especially through the individual administration thereof.

The invention is further described in the accompanying drawings, wherein:

FIG. 1 is a chart of the total amount of trace element released plotted against time for one tablet in accordance with the invention;

FIG. 2 is a similar chart for another tablet; and

FIG. 3 is a plot of the hemoglobin content in the blood of animals treated with the tablets of FIGS. 1, 2 and of untreated controls.

The drawings will be further discussed in connection with the following examples:

EXAMPLE 1

Finely powdered iron-II-fumarate is thoroughly mixed with 15% methylcellulose (sold by Lehmann & Voss, Hamburg, under the trademark "Avicel") and 1% magnesium stearate, by weight, and pressed into pills 18 mm long and 5 mm in diameter in a tablet press using a die of oblong shape. These tablets are sprayed in a spraying drum, at a temperature in the treatment chamber of 50°C, with a dispersion of polyvinylidene chloride and polyacrylic acid ester comprising 55% solids by weight, until the coating formed by evaporation amounts to about 0.5 wt.-%. The best coating thickness can be adjusted by subjecting the product to the iron release test described hereinafter.

In testing the effectiveness of the above-mentioned preparation it is necessary to simulate the physiological chemical conditions in the animal stomach. This is done experimentally by exposing an oblong tablet to an HCl solution of pH 1.5 at 37°C with a gently circulating movement of the liquid. The amount of iron released is determined analytically several times within the period of 21 days which is important to the suckling pig. This iron release test, whose results are given in FIG. 1, shows that a uniform release of iron ions is assured by the tablet.

EXAMPLE 2

Iron-II-diphosphate is obtained by precipitation from an iron-II-sulfate solution with a tetrasodium diphosphate solution of a pH of 3 to 4. After separation and drying of the precipitate, the powdered material, having an iron content of about 38% by weight, is mixed with equal weight-parts of powdered iron. In a tablet press using a die of oblong shape, this powder mixture is pressed, after the addition of 1 wt.-% of magnesium stearate, into pills 18 mm long and 5 mm in diameter. The tablet composition has an iron content of approximately 63.5% by weight.

The iron release test in vitro described in Example 1 gives the results shown in FIG. 2, which again prove a constant release of iron ions.

ANIMAL EXPERIMENTS

The results of animal experiments shown in FIG. 3 are decisive proof of the effectiveness of the sustained-release boluses of the invention in the prophylaxis and treatment of dietary iron deficiency anemia. One group of twelve uniformly developed suckling pigs from four litters remained untreated (Curve 3). A second and third group of the suckling pigs received orally the two types of preparations of Examples 1 (Curve 1) and 2 (Curve 2). After 4, 7, 14 and 21 days the hemoglobin concentration in the blood was determined. The effectiveness of the orally administered iron preparations is proven by the increase in the hemoglobin content at the end of 21 days. The blood of treated animals (Curves 1 and 2) has a considerably higher hemoglobin content than that of the untreated animals (Curve 3) after a few days, the hemoglobin concentration being an indication of the presence and extent of the anemia.

As noted, composition of the tablet can vary and, when plastics are employed either as a homogeneously distributed matrix or as a covering, other monomers than those enumerated above can also be employed, either as homopolymers or copolymers, the molecular weights being appropriately chosen. Similarly, the minimum dimension of the tablet will depend upon the particular animal being treated and its size. For most purposes a minimum dimension of about 3 mm is suitable, i.e. a spherical or cylindrical tablet whose transverse cross-section has a dimension of at least the indicated size.

It will be appreciated that the instant specification and examples are set forth by way of illustration and not limitation, and that various modifications and changes may be made without departing from the spirit and scope of the present invention.

We claim:

1. A sustained-action tablet for treating iron deficiency comprising a tablet containing iron-II-fumarate or iron-II-diphosphate + iron powder and of a composition such that it releases said trace element over a prolonged period of time, said tablet being about 18 mm long and having a minimum transverse dimension of at least about 3 mm and including an acid-resistant physiologically compatible sustained release plastic coating which ensures the tablet maintains its size during the sustained release, whereby said tablet is not eliminated prematurely through the pylorus of a suckling piglet yet is eliminated when the piglet pylorus opening has increased in size due to the growth of the pig.

2. The tablet according to claim 1, wherein said tablet further contains at least one trace element selected from the group consisting of manganese, cobalt, zinc, copper, selenium and fluorine.

3. The tablet according to claim 2, wherein said plastic is selected from the group consisting of copolymers of vinylidene chlorine, an acrylic acid ester, vinyl chloride and vinyl propionate.

4. The process for treating iron deficiency in a piglet over a prolonged period of time comprising orally administering to said piglet a tablet according to claim 1.

5. The process of claim 4, wherein said tablet further contains at least one trace element selected from the group consisting of manganese, cobalt, zinc, copper, selenium and fluorine.

6. The process of claim 4, wherein said plastic is selected from the group consisting of copolymers of vinylidene chlorine, and acrylic acid ester, vinyl chloride and vinyl propionate.

7. The process of claim 4, wherein said tablet has a rounded oblong shape, is about 18 mm long and about 5 mm in diameter, is coated with about 0.5 weight percent of a copolymer of vinylidene chloride and acrylic acid ester and consists essentially of finely powdered iron-II fumarate mixed with about 15% of methylcellulose and about 1% of magnesium stearate by weight.

* * * * *